United States Patent [19]

Hellstrom et al.

[11] Patent Number: 5,840,854
[45] Date of Patent: Nov. 24, 1998

[54] MONOCLONAL ANTIBODY BR110 AND USES THEREOF

[75] Inventors: Karl Erik Hellstrom; Ingegerd Hellstrom, both of Seattle; Ursula Garrigues, Bainbridge Island, all of Wash.; Stephen McAndrew, Newtown, Pa.; Hans Marquardt, Mercer Island, Wash.

[73] Assignee: Bristol-Myers Squibb Company, Princeton, N.J.

[21] Appl. No.: 726,528

[22] Filed: Oct. 7, 1996

Related U.S. Application Data

[60] Provisional application No. 60/005,641, Oct. 19, 1995.
[51] Int. Cl.$^6$ .................................................. A61K 31/395
[52] U.S. Cl. .................................. 530/387.7; 530/387.3; 530/388.2; 530/391.3; 530/391.7; 435/328; 435/330; 435/172.2; 424/133.1; 424/138.1; 424/155.1; 424/181.1
[58] Field of Search ............................ 530/387.7, 387.3, 530/388.2, 391.3, 391.7; 435/69.1, 328, 330, 172.2; 424/138.1, 133.1, 155.1, 181.1

[56] References Cited

U.S. PATENT DOCUMENTS 5,185,254 2/1993 Linnenbach .......................... 435/172.3

FOREIGN PATENT DOCUMENTS

| 0 376 746 | 7/1990 | European Pat. Off. . |
| WO 90/12592 | 11/1990 | WIPO . |
| WO 93/08298 | 4/1993 | WIPO . |

OTHER PUBLICATIONS

Marglin et al Ann Rev Biochem vol. 39: 841–866, 1970.
Fanger et al FASEB Journal vol. 4 2846–2849, 1990.
Paul, WE Fundamental Immunology Third Edition p. 242, 1993.
Osband et al Immunology Today vol. 11 No.6:193–195, 1990.
Waldmann Science vol. 252:1657–1661, 1991.
Dillman Annals of Internal Medicine vol. 111 592–603, 1989.
Seaver Genetic Engineering vol. 14 (14) p. 10 and 21, 1994.
Stein et al Cancer Research vol. 50 1330–1336, 1990.
Fradet et al Proc Nat Acad Sci USA vol. 81 224–228, Jan. 1984.
Miotti et al int J Cancer vol. 39 297–303, 1987.
Alberti et al Hybridoma vol. 11 No. 5 539–545, 1992.
Fornaro et al, Int J Cancer vol. 62 610–618, 1995.
Lerner et al Nature vol. 229:592–596, 1992.
Galfre et al Methods in Enzymology vol. 73 1–46, 1981.
Reichmann et al Nature vol. 332 323–327, Mar. 1988.
Blakey et al Monoclonal Antibody Therapy Prog Allergy Basel Karger vol. 45 50–90, 1988.
Zuckier et al Seminars in Nuclear Medicine vol. XIX 166–186, Jul. 1989.
Bird et al Science vol. 241 423–426, Oct. 1988.
Casalini, P. et al. (1993) A critical comparison of three internalization assays applied to the evaluation of a given mAb as a toxin–carrier candidate, Cancer Immunol. Immunother. 37:54–60.
Herlyn, D. et al. (1986) Anti–idiotypic antibodies bear the internal image of a human tumor antigen, Science 232:100–102.
Herlyn, D. et al. (1986) Hybridoma, 5:S3–S10.
Linnenbach, A.J. et al. (1989) Sequence investigation of the major gastrointestinal tumor–associated antigen gene family, GA733, Proc. Natl. Acad. Sci. USA 86:27–31.
Szala, S. et al. (1990) Molecular cloning of a cDNA for the carcinoma–associated antigen GA733–2, Proc Natl. Acad. Sci. USA 87:3542–3546.
Rakowicz–Szulczynska, E.M. et al. (1992) Nuclear translocation of monoclonal antibody directed against cell–surface carbohydrate Y determinant, American Journal of Pathology 141(4):937–947.
Stein, R. et al., "Characterization of Cluster 13: The Epithelial/Carcinomas Antigen Recognized by Mab RS7", Internation Journal of Cancer: Supplement, 1994, vol. 8, pp. 98–102.
De Leij, L. et al., "SCLC–Cluster–2 Antibodies Detect the Pancarcinoma/Epithelial Glycoprotein EGP–2", International Journal of Cancer: Supplement, 1994, vol. 8, pp. 60–63.
Stein, R. et al., "Specificity and Properties of Mab RS7–3G11 and the Antigen Defined by This Pancarcinoma Monoclonal Antibody", Internation Journal of Cancer, Dec. 2, 1993, vol. 55, pp. 938–946.
Friedman P. N. et al., "Antitumor Activity of the Single Chain Immunotoxin BR96 sFv–PE40 Against Established Breast and Lung Tumor Xenografts", Journal of Immunology, Apr. 1993, vol. 150, No. 7, pp. 3054–3061.

*Primary Examiner*—Sheela Huff
*Assistant Examiner*—Julie E. Reeves
*Attorney, Agent, or Firm*—Merchant, Gould, Smith, Edell, Welter, & Schmidt

[57] ABSTRACT

The present invention provides internalizing ligands (i.e., BR110 ligands) which specifically recognize and bind the BR110 antigen. After binding the antigen, the ligand and antigen form a complex. As a complex, the antigen can be detected using well known and developed methods and commercial systems.

22 Claims, 1 Drawing Sheet

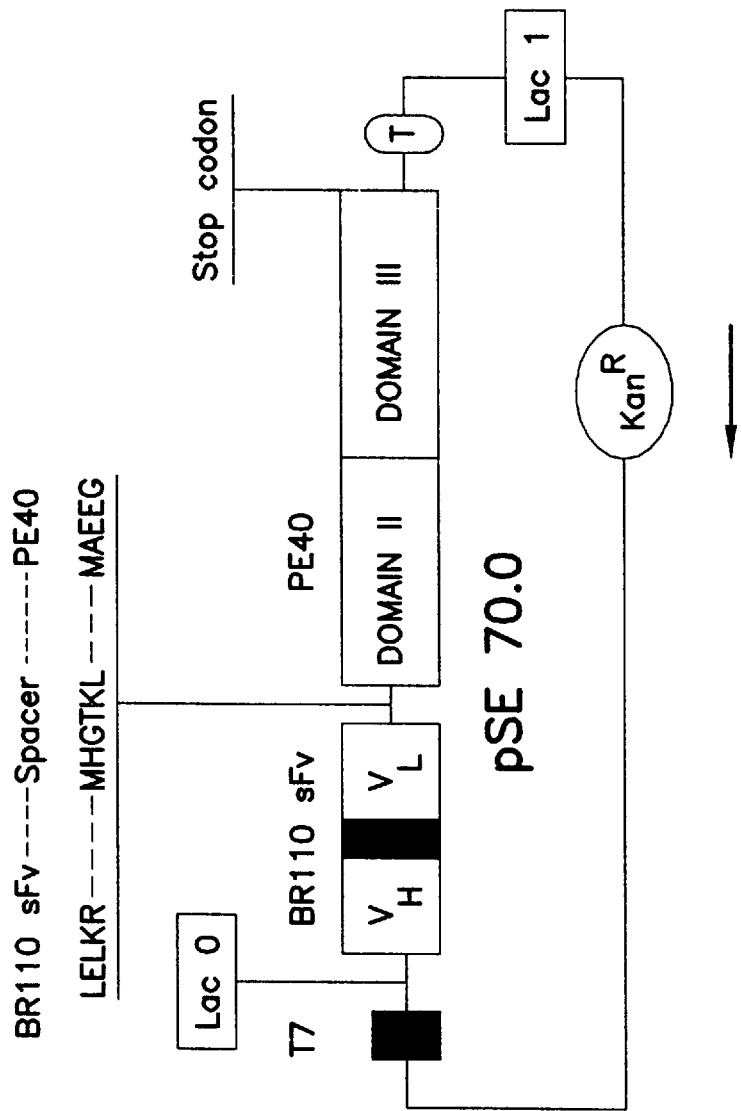

MONOCLONAL ANTIBODY BR110 AND USES THEREOF

This application is claiming the benefit of a provisional application for patent filed under 35 U.S.C. §111(b), having U.S. Ser. No. 60/005,641, filed Oct. 19, 1995, the contents of which are incorporated by reference.

Throughout this application various publications are referenced. The disclosures of these publications in their entireties are hereby incorporated by reference into this application in order to more fully describe the state of the art to which this invention pertains.

BACKGROUND OF THE INVENTION

Cancer includes a broad range of diseases which affect one in four people worldwide. Clearly, in terms of the number of people affected, cancer poses a serious medical concern. Because of the seriousness of the problem and its impact on society, effective therapeutic and diagnostic agents directed against cancer are valued at a premium. Antibodies to human tumor-associated antigens are recent technological achievements which promise to be important therapeutic and diagnostic agents against certain cancers.

Antibodies to human tumor associated antigens are well known and well described. One such tumor associated antigen is designated the GA733-2 antigen. The GA733-2 antigen has a molecular weight of about 34kD–40kD and is a member of a family of GA733 antigens (Linenbach et al. PNAS USA 86:27–31 (1989)). The biological function of the GA733-2 antigen is unknown (International Publication No. WO 93/0829, published Apr. 29, 1993).

Using the DNA probe from GA733-2, researchers were able to screen a genomic library and isolate a homologous sequence designated GA733-1. From the GA733-1 gene, researchers were able to express the antigen. However, no one had determined whether the antigen was a tumor associated antigen.

The fact that the GA733-1 gene was isolated from a genomic library further added to the uncertainty whether the gene and the antigen encoded thereby were generally found on normal cells, tumor cells, or both and the frequency in which they were found. The molecular weight and function of the GA733-1 antigen are unknown. The GA733-1 antigen contains multiple epitopes, and a segment of the DNA which codes for the GA733-1 is known (U.S. Pat. No. 5,185,254, supra).

The GA733-2 antigen is recognized by a monoclonal antibody designated MoAb GA733 (also known as GA733-2 antibody) (Herlyn, et al. Hybridoma, 5:S3–S10 (1986)). MoAb GA733 has been evaluated for the diagnosis and therapy of human gastrointestinal tumors.

It exhibits tumoricidal characteristics. Despite the fact that GA733-1 and GA733-2 share 49% homology in amino acid sequence (U.S. Pat. No. 5,185,254, issued Feb. 9, 1993), MoAb GA733 binds the GA733-2 antigen but does not bind the GA733-1 antigen. MoAb GA733 does bind normal epithelial cells.

In addition to GA733, several independently derived mAbs such as CO17-1A, M77, M79, 323/A3, all recognize and bind the GA733-2 antigen (International Publication No. WO 93/0829, supra). Monoclonal antibody CO17-1A (also known as the 17-1A antibody) binds to GA733-2 antigen but does not recognize and bind the GA733-1 antigen.

Presently, there are no known monoclonal antibodies directed against the GA733-1 antigen. The BR110 ligands of the invention recognize and bind the GA733-1 antigen and are internalized by cells after binding to antigen. Further, the BR110 ligands of the invention appear to exhibit tumoricidal activity.

Internalizing antibodies are rare. Presently, there is a need in therapeutic applications for such "internalizing" antibodies, i.e., antibodies that are easily taken up by the tumor cells to which they bind. Such antibodies, for example, can be coupled to biological and/or chemical agents that are only effective when transported into the cell.

SUMMARY OF THE INVENTION

The BR110 ligands of the invention, e.g., BR110 monoclonal antibodies, meets the therapeutic and diagnostic needs discussed hereinabove.

BR110 ligands share common characteristics. For example, each BR110 ligand specifically recognizes and binds the BR110 antigen and is directed to at least a portion of the epitope to which the monoclonal antibody BR110 (ATCC No. 11698) is directed.

In one embodiment of the invention, the BR110 ligand is the monoclonal antibody BR110 (ATCC No. 11698). Further, another embodiment of the BR110 ligand of the invention is a human/murine recombinant antibody, the antigen-binding region of which competitively inhibits the immunospecific binding of monoclonal antibody BR110 produced by hybridoma HB 11698 to its target antigen. Additionally, the invention provides uses for the BR110 ligands of the invention.

BRIEF DESCRIPTION OF THE FIGURE

FIG. 1 is a graphic representation of the plasmid pSE 70.0.

DETAILED DESCRIPTION OF THE INVENTION

DEFINITIONS

As used in this application, the following words or phrases have the meanings specified.

As used herein "ligand" includes an intact antibody molecule and any molecule having at least an antigen-binding region or portion thereof (i.e., the variable portion of an antibody molecule), e.g., an Fv molecule, Fab molecule, Fab' molecule, F(ab')$_2$ molecule, a bispecific antibody, a fusion protein, or any genetically engineered molecule which specifically recognizes and binds the BR110 antigen.

As used herein "antigen-binding region" means a portion of the molecule which recognizes the target antigen.

As used herein "competitively inhibits" means being able to recognize and bind a determinant site to which the monoclonal antibody BR110 is directed using conventional reciprocal antibody competition assays. (Belanger L., Sylvestre C. and Dufour D. (1973), Enzyme linked immunoassay for alpha fetoprotein by competitive and sandwich procedures. *Clinica Chimica Acta* 48, 15).

As used herein "target antigen" is the antigen GA733-1 or portions thereof.

As used herein "joined" means to link two or more generally separate entities or segments through a covalent linkage or a non-covalent linkage.

As used herein "functionally active" means that portion of the molecule which is able to recognize and bind its target.

As used herein "biologically or chemically active molecule" means any biological or chemical molecule which can inhibit or arrest cell growth or otherwise act to the detriment of the cell.

As used herein, an "immunoconjugate" means any molecule or ligand such as an antibody chemically or biologically linked to a cytotoxin, a radioactive agent, enzyme, toxin, an anti-tumor drug or a therapeutic agent. The antibody may be linked to the cytotoxin, radioactive agent, anti-tumor drug or therapeutic agent at any location along the molecule so long as it is able to bind its target. Examples of immunoconjugates include antibody toxin chemical conjugates and antibody-toxin fusion proteins.

As used herein, an "effective amount" is an amount of the antibody, immunoconjugate, or recombinant molecule which kills target cells or inhibits the proliferation thereof.

As used herein, a "fusion protein" means any chimeric protein wherein an antigen binding region is connected to a biologically active molecule, e.g., toxin, enzyme, or protein drug.

In order that the invention herein described may be more fully understood, the following description is set forth.

A. THE LIGANDS OF THE INVENTION

The present invention provides internalizing ligands (i.e., BR110 ligands) which specifically recognize and bind the BR110 antigen.

The ligand of the invention may be in any form as long as it has an antigen-binding region which competitively inhibits the immunospecific binding of monoclonal antibody BR110 produced by hybridoma HB 11698 to its target antigen. Thus, any recombinant proteins (e.g., fusion proteins wherein the antibody is combined with a second protein such as a lymphokine or a tumor inhibitory growth factor) having the same binding specificity as the BR110 antibody fall within the scope of this invention.

In one embodiment of the invention, the ligand is a monoclonal antibody BR110. The hybridoma which produces the monoclonal antibody BR110 has been deposited under the requirements of the Budapest Treaty on Aug. 10, 1994 with the American Type Culture Collection ("ATCC") 10801 University Boulevard, Manassas, Va. 20110-2209and has been identified as ATTC Acession No.: HB 11698.

In other embodiments, the ligand is a Fv molecule (such as a single chain Fv molecule), a Fab molecule, a Fab' molecule, a F(ab')2 molecule, a fusion protein, a bispecific antibody, a heteroantibody or any recombinant molecule having the antigen-binding region of the BR110 antibody. The ligand of the invention is directed to the epitope to which monoclonal antibody BR110 (ATCC No. 11698) is directed.

In one embodiment of the invention, the ligand of the invention is directed to the epitope to which the monoclonal antibody BR110 is directed and exhibits an affinity of at least about $2\times10^8$ liters/mole to its target or, in the case of multivalent antibodies, an avidity that is at least as high as that which would result from the binding of a bivalent antibody of affinity $10^8$ liters/mole to an antigen. Different affinities are possible and are encompassed by the invention.

The ligand of the invention may be modified, i.e., by amino acid modifications within the molecule, so as to produce derivative molecules. Chemical modification may also be possible.

Derivative molecules would retain the functional property of the polypeptide, namely, the molecule having such substitutions will still permit the binding of the polypeptide to the GA733-1 antigen or portions thereof.

These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein.

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

B. METHODS OF MAKING THE LIGANDS OF THE INVENTION

Ligands of the invention include (1) monoclonal antibodies and fragments thereof, (2) recombinant molecules having at least an antigen-binding region or portion thereof, e.g., an Fv molecule, Fab molecule, Fab' molecule, $F(ab')_2$ molecule, a bispecific antibody, a fusion protein, or (3) any genetically engineered molecule, all of which specifically recognizes and binds the BR110 antigen.

Monoclonal antibodies of the invention

Hybridomas producing the monoclonal antibodies of the present invention are produced following general procedures described by Kohler and Milstein ((1975) Continuous culture of fused cells secreting antibody of defined specificity. *Nature* 256, 495–497) with some modifications (M. Yeh et al., "Cell Surface Antigens Of Human Melanoma Identified By Monoclonal Antibody", *Proc. Natl. Acad. Sci. U.S.A.,* 76(6):297–31 (1979); and Yeh et al., "A Cell-Surface Antigen Which is Present In the Ganglioside Fraction And Shared By Human Melanomas", *Int. J. Cancer,* 29:269–75 (1982)). In this procedure, hybridomas are prepared by fusing antibody producing cells (typically spleen cells of mice previously immunized with an immunogen) to cells from an immortal tumor cell line using somatic cell hybridization procedures.

The novel monoclonal antibodies described herein were generated by immunizing mice with neuraminidase pretreated H3922 human breast carcinoma cells. For immunization with H3922 human breast carcinoma cells, the animals are inoculated intraperitoneally at least once with $10^7$ cells of the immunogen. The animals are then boosted two or more times with immunogen. Spleens are harvested from the animals several days after the last boost, and a spleen cell suspension is prepared for fusion using known fusion techniques with murine myeloma cells.

The hybridomas resulting from the fusion process are allowed to grow. Thereafter, the resulting supernatants are screened using immunoassay procedures to detect antibodies present in the supernatants capable of binding to the specific antigen (Hardy RR (1986) Purification and characterization of monoclonal antibodies. In: Weir, D. M. and Herzenberg, L. A. (eds) *Handbook of Experimental Immunology,* 4th edn, Vol. 1, p. 13. Oxford: Blackwell Scientific Publications; Engvall, E. and Perlmann, P. (1971) Enzyme linked immunosorbent assay (ELISA): quantitative assay of immunoglobulin G. *Immunochemistry* 8, 871).

Recombinant proteins of the invention

It would be routine to make recombinant proteins capable of binding to the same antigenic determinant as the BR110 antibody. Identifying recombinant proteins which recognize the same binding site merely involves setting up competition assays in which the antibodies of the present invention compete with another antibody for the target (Belanger, L., Sylvestre, C. and Dufour, D. (1973) Enzyme linked immunoassay for alpha fetoprotein by competitive and sandwich procedures. *Clinica Chimica Acta* 48, 15). Competition assays are routine and their protocols are well established (E. Harlow and D. Lane, eds., "Antibodies a laboratory manual" 1988, pages 567–577).

Class, isotype and other variants of the antibody of the invention having the antigen-binding region of the BR110 antibody may be constructed using recombinant classswitching and fusion techniques which are known in the art. (Winter, G. and Milstein, C. (1991) Man-made antibodies. *Nature* 349, 293–299. Pluckthun, A. (1991) Antibody engineering: advances from the use of *Escherichia coli* expression systems. *Bio/Technology* 9, 545–551. Moore, G. P. (1989) Genetically engineered antibodies. *Clinical Chemistry* 35, 1849–1853).

The present invention provides BR110 fusion proteins. General techniques for construction of expression vectors for fusion proteins are well established (Ernst Winnacker, "From Genes to Clones: Introduction to Gene Technology" Chapter 7, 1987 at pages 239–317). For example, a general approach for the construction of expression vectors directing the synthesis of fusion proteins is as follows.

The starting material can be a cDNA clone, wherein the gene of interest has been removed from a vector. Using methods known in the art a restriction site is positioned close to a start codon. The next step is a digestion step which would cut DNA fragments asymmetrically. The mixture of DNA fragments obtained is then cloned into a vector. Of course, a cleavage site must be present within the polylinker of the chosen vector. Since a wide spectrum of vectors is available, it would not be difficult to find a suitable vector containing the desired cleavage site. Once a suitable clone is identified, the cleavage site can be used for the insertion of the gene of interest, which can be obtained from the original cDNA clone.

The present invention provides chimeric BR110 proteins. Making chimeric BR110 protein capable of binding to the same antigenic determinant as the BR110 antibody is routine (Morrison, S. L., Johnson, M. J., Herzenberg, L. A., and Oi, V. T. (1984). Chimeric human antibody molecules: Mouse antigen-binding domains with human constant region domains. Proc. Natl. Acad. Sci. U.S.A. 81, 6851–6855, Morrison, S. L. (1985). Transfectomas provide novel chimeric antibodies. Science 229, 1202–1207).

Genetic engineering can be used to create chimeric immunoglobulins by (1) combining the rodent variable heavy gene segment ($V_H$) with human heavy-chain constant region gene segments to make the heavy-chain gene construct, (2) connecting the rodent variable light ($V_L$) gene segment with a human constant light ($C_L$) exon to create the light-chain gene construct, and (3) transfecting both the heavy- and light-chain gene constructs into a myeloma cell line (Fell et al., in *Proc. Natl. Acad. Sci. U.S.A.* 86:8507–8511 (1989); Morrison, S. L., Johnson, M. J., Herzenberg, L. A., and Oi, V. T. (1984). Chimeric human antibody molecules: Mouse antigen-binding domains with human constant region domains. Proc. Natl. Acad. Sci. U.S.A. 81:6851–6855)

The principle, any rodent variable domain can be paired with any human constant region isotype so that the optimal combination of antigenic specificity and effector functions (such as complement fixation and ADCC (antibody-dependent cell-mediated cytotoxicity) can be selected (Morrison, S. L. (1985). Transfectomas provide novel chimeric antibodies. *Science* 229, 1202–1207).

If necessary, fine-tuning of the constructs can be accomplished by introducing point mutations in the variable region gene segments that alter the affinity of the chimeric antibody for its ligand (Kunkel, T. A., 1985, *Proc. Natl. Acad. Sci. U.S.A.*, 32;488–492; Kunkel, T. A., et al., 1987, *Methods Enzymol.* 154:367–382).

In order to reduce or eliminate any murine characteristics of the BR110 ligand, humanized versions thereof can be produced using molecular manipulations and transfectoma technology (Co, M. S., Deschamps, M., Whitley, R. J., and Queen, C. (1991). Humanized antibodies for antiviral therapy. *Proc. Natl. Acad. Sci. USA* 88, 2869–2873).

Different human heavy-chain isotypes can be chosen for the humanized antibody, depending on the desired therapeutic effect. For instance, when destruction of the target cell is desired, the human IgG1 constant region can be chosen since it is recognized by FcγR I, FcγR II, and FcγR III and mediates ADCC (Anderson, C. L., and Looney, R. J. (1986). Human leukocyte IgG Fc receptors. *Immunol. Today* 7, 264–266).

Chimeric antibodies having different effector functions have been produced by linking different sequences to those encoding the antigen binding region. These different sequences include enzymes (Neuberger et al., *Nature* 312:604 (1984)), immunoglobulin constant regions from another species and constant regions of another immunoglobulin chain (Sharon et al., *Nature* 309:364 (1984); Tan et al., *J. Immunol.* 135:3565–3567 (1985)).

In other situations, such as in diagnostic imaging, antibody-receptor blocking, or antibody-mediated drug delivery, isotypes that bind Fc receptors poorly (or not all) and/or are relatively ineffective at complement-mediated lysis (such as IgG2, IgG4, or IgA) can be the isotypes of choice.

Molecular manipulations and transfectoma technology are popular means to "humanize" rodent antibodies with interesting specificities. These rodent-human chimeric antibodies are expected to be less antigenic and more useful in human therapy (Co, M. S., Deschamps, M., Whitley, R. J., and Queen, C. (1991). Humanized antibodies for antiviral therapy. *Proc. Natl. Acad. Sci. USA* 88, 2869–2873).

In general, an example of one procedure which can be used to produce chimeric antibodies involve the following steps:

a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) can be in either the cDNA or genomic form;

b) cloning the gene segments encoding the constant region or desired part thereof;

c) ligating the variable region with the constant region so that the complete chimeric antibody is encoded in a transcribable and translatable form;

d) ligating this construct into a vector containing a selectable marker and gene control regions such as promoters, enhancers and poly(A) addition signals;

e) amplifying this construct in bacteria;

f) introducing this DNA into eukaryotic cells (transfection), most often mammalian lymphocytes;

g) selecting for cells expressing the selectable marker;

h) screening for cells expressing the desired chimeric antibody; and k) testing the antibody for appropriate binding specificity and effector functions.

Other procedures for producing chimeric antibodies are well known in the art.

Identifying chimeric antibodies which recognize the binding site of the BR110 antibody is routine, e.g., by competition assays (E. Harlow and D. Lane, eds., "Antibodies a laboratory manual" 1988, pages 567–577).

The BR110 monoclonal antibody of the invention can also be made by chemically conjugating the variable regions of BR110 ligand and a human constant region by chemical means, e.g., conjugation with (2) disulfide generating agents such as 3-(2-pyridyldithio)propionate (SPDP), (2) thioether linkages, (3) activated chlorambucil, (4) acid labile and photocleavable cross-linkers, and (5) avidin biotin linkage (Stevenson, F. K., Bell, A. J., Cusack, R., Hamblin, T. J., Slade, C. J., Spellerberg, M. B., and Stevenson, G. T. (1991). Preliminary studies for an immunotherapeutic approach to the treatment of human myeloma using chimeric anti-CD38 antibody. *Blood* 77, 1071–1079; S. Wong "Chemistry of Protein Conjugation and Cross-Linking" (1993) CRC Press, Inc.).

Other methods for producing the ligand of the invention are possible (Liu, A. Y., Robinson, R. R., Murray, E. D. Jr., Ledbetter, J. A., Hellstrom, I., and Hellstrom, K. E. (1987a). Production of a mouse-human chimeric monoclonal antibody to CD20 with potent Fc-dependent biologic activity. *J. Immunol.* 139, 3521–3526).

The present invention also provides bispecific BR110 monoclonal antibodies. Making bispecific BR110 monoclonal antibodies capable of binding to the same antigenic determinant as the BR110 antibody is routine (Haber et al., 1990; Wels, W., Harwerth, I. M., Zwickl, M., Hardman, N., Groner B., Hynes, N. E. (1992) Construction, bacterial expression and characterization of a bifunctional single-chain antibody phosphatase fusion protein targeted to the human ERBB-2 receptor. Biotechnology 10:1128–1132; A. Traunecker et al. (1991) EMBO Journal 10(12):3655–3659). BR110 antibody fragments of the invention BR110 antibody fragments include Fv molecule, Fab molecule, Fab' molecule, F(ab')$_2$ molecule.

Murine BR110 ligand ATCC No. 11698 can be purified by affinity chromatography from murine ascites fluid. F(ab')$_2$ fragments can be generated by digesting purified BR110 monoclonal antibody with pepsin according to Lamoyi, "Preparation of F(ab')$_2$ Fragments from Mouse IgG of Various Subclasses", *Meth. Enzymol.* 121:652–663 (1986).

Alternatively, F(ab')$_2$ fragments can be produced through genetic engineering means using routine methodologies (Mayforth R. D., Quintans, J. (1990) Current Concepts: Designer and catalytic antibodies. New Eng. J. Med. 323:173–178; Waldmann, T. A. (1991) Monoclonal antibodies in diagnosis and therapy. Science 252:1657–1662; Winter, G., Milstein, C. (1991) Man-made Antibodies. Nature 349:293–299; Morrison, S. L. (1992) In Vitro antibodies: strategies for production and application. Ann. Rev. Immunol. 10:239–266; Haber et al., 1990; Wels, W., Harwerth, I. M., Zwickl, M., Hardman, N., Groner B., Hynes, N. E. (1992) Construction, bacterial expression and characterization of a bifunctional single-chain antibody phosphatase fusion protein targeted to the human ERBB-2 receptor. Biotechnology 10:1128–1132; A. Traunecker et al. (1991) EMBO Journal 10(12):3655–3659).

Binding of whole BR110 ligand can be distinguished from binding of F(ab')$_2$ fragments by using horseradish peroxidase (HRP)-conjugated protein A which binds to the whole antibody but not the F(ab')$_2$ fragments.

BR110 Fab fragments can be produced through proteolytic cleavage of the intact BR110 antibody using, e.g., papain (Parham, P., 1986 Preparation and purification of active fragments from mouse monoclonal antibodies. In "Handbook of experimental immunology. In four volumes" Volume 1 "Immunochemistry" (Eds. D. W. Weir et al.) pages 14.1–14.23, Blackwell Scientific Publishers, Oxford.) Parham P. (1986) Preparation and purification of active fragments from mouse monoclonal antibodies. In: Weir, D. M. and Herzenberg, L. A. (eds) *Handbook of Experimental Immunology*, 4th edn, Vol. 1, p. 14. Oxford: Blackwell Scientific Publications).

Alternatively, Fab fragments can be produced through genetic engineering means using routine techniques (Huse et al. 1989 "Generation of a large combinatorial library of the immunoglobulin receptor in phage lambda" Science 246:1275–1281).

PROTOCOL FOR CONSTRUCTING AND PURIFYING BR110 LIGAND CONJUGATES AND FUSION PROTEINS

The invention provides BR110 immunoconjugates comprising a BR110 ligand joined to at least a portion of a biologically or chemically active molecule (Batra et al., *Proc. Natl. Acad. Sci. USA* 86:8545–8549 (1989); Kondo et al., *J. Biol. Chem.* 263:9470–9475 (1988); and Batra et al., *Proc. Natl. Acad. Sci. USA* 86:8545–8549 (1989). The biologically or chemically active molecule, such as a cytotoxic agent, can inhibit or arrest cell growth or otherwise act to the detriment of the cell. In accordance with the practice of the invention, biologically or chemically active molecules include, but are not limited to, an enzyme, lymphokine, a toxin, a paramagnetic isotope, biotin, a fluorophore, a chromophore, a heavy metal, a radioisotope, or a chemotherapeutic agent. Suitable examples of toxins include, but are not limited to, Pseudomonas exotoxin, ricin, bryodin, and diphtheria toxin. Additional examples include bleomycin, dactinomycin, daunorubicin, doxorubicin, mitoxantron, mitomycin, cisplatin, and procarbazine.

Genetic engineering techniques known in the art can be used as described herein to prepare recombinant immunotoxins produced by ligating a DNA sequence encoding an antigen binding region of BR110 with a DNA sequence encoding a biologically or chemically active molecule at the DNA level and expressing in a transformed host cell the cytotoxic molecule as a recombinant protein. Recombinant immunotoxins are homogenous molecules that retain the specificity of the cell binding portion of the BR110 antibody with the cytotoxic potential of the toxin (Kondo et al., *J. Biol. Chem.* 263:9470–9475 (1988); Siegall et al., *Proc. Natl. Acad. Sci. USA* 85:9738–9742 (1988) Pastan, I., and FitzGerald, D. (1991). Recombinant toxins for cancer treatment. *Science* 254, 1173–1177. Pastan, I., Willingham, M. C., and FitzGerald, D. J. (1986). Immunotoxins. *Cell* 47, 641–648).

Recombinant immunoconjugates, particularly single-chain immunoconjugates have an advantage over drug/antibody conjugates in that they are more readily produced than these conjugates, and generate a population of homogenous molecules, i.e., single polypeptides composed of the same amino acid residues (Trail, P. A., et al. Cure of xenografted human carcinomas by BR96-doxorubicin immunoconjugates. Science, 261:212–215, 1993). When the biologically or chemically active molecule is a toxin or drug, the conjugate is more potent than its non-conjugated counterpart.

D. USES OF THE LIGANDS OF THE INVENTION

The present invention provides a method of detecting BR110 antigen in tissue sections from a subject. In accordance with the practice of this invention, the subject can be a human, equine, porcine, bovine, murine, canine, feline, or avian subject. Other warm blooded animals are also included.

This method comprises contacting the tissue sections with the monoclonal antibody of the invention. The conditions under which the tissue sections are contacted with the monoclonal antibody of the invention are such that binding occurs so that a complex is formed. After formation of the complex, the antigen can be detected using well known and developed methods and commercial systems (Gatter, K. C., Falini, B. and Mason, D. Y. (1984) The use of monoclonal antibodies in histopathological diagnosis. Recent Advances in Histopathology 12, 35; Boekmann, E., Baum, R. O., Schuldes, H., Kramer, W., Hertel, A., Baew-Christow, T., Hanke, P., Jonas, D. and Hor, G. (1990) Tumour imaging of bladder carcinomas and their metastases with $^{111}$In-labelled monoclonal anti-CEA antibody BW 431/26. British Journal of Cancer 62 (Suppl.), 81).

In one embodiment of the invention, the tissue section is breast tissue and the neoplastic tissue is a breast carcinoma. Alternatively, the tissue is colon tissue and the neoplastic tissue is adenocarcinoma. Further, the tissue is lung tissue and the neoplastic tissue is lung carcinoma. Also, in another embodiment, the tissue is ovarian tissue and the neoplastic tissue is ovarian carcinoma.

Generally, the tissue sections are of a tissue in which normal tissue is characterized by the absence of low levels of BR110 antigen and neoplastic tissue is characterized by the presence of high levels of BR110 antigen.

In accordance with the practice of the invention, the monoclonal antibody bound to the tissue sections can be detected directly using a labeled marker attached to the antibody. Alternatively, the monoclonal antibody bound to the tissue sections can be detected by contacting the monoclonal antibody with a second antibody. The second antibody can be labeled with a detectable marker. After contact, the monoclonal antibody bound to the tissue sections forms a complex with the second antibody. The complex is detected by detecting the second antibody so bound.

The present invention additionally provides a method of determining a difference in the amount of distribution of BR110 antigen in tissue sections from a neoplastic tissue to be tested relative to the amount and distribution of BR110 antigen in tissue sections from a normal tissue. This method comprises contacting both the tissue to be tested and the normal tissue with the monoclonal antibody of the invention so that detection can be effected as described hereinabove. After detection is effected, a determination of the difference in the amount and distribution of BR110 antigen can be made. This determination is a quantitative determination, i.e., counting the number of antigens so detected, or a visual determination, i.e., determining which sample is darker or lighter, or has a particular color etc.

The invention further provides a method of diagnosing a neoplastic condition in a subject. In one embodiment, this method comprises obtaining from the subject a sample of tissue. The tissue sample is then contacted with the antibody of the invention so that the presence of the BR110 antigen in such tissue sections will cause the formation of a complex between the antibody and the antigen. The presence of the complex is detected. If a higher level of the complex is detected in the sample than in normal tissue, then that level is indicative of a neoplastic condition and further tests may be warranted.

Alternatively, detection of tumor can be achieved using a biological fluid sample so as to detect human carcinoma in a subject. Serologic diagnostic techniques involve the detection and quantitation of tumor-associated antigens that have been secreted or "shed" into the serum or other biological fluids of patients thought to be suffering from carcinoma. Such antigens can be detected in the body fluids using techniques known in the art such as radioimmunoassays (RIA) or enzyme-linked immunosorbent assays (ELISA) wherein an antibody reactive with the "shed" antigen is used to detect the presence of the antigen in a fluid sample (Uotila et al., "Two-Site Sandwich ELISA With Monoclonal Antibodies To Human AFP", J. Immunol. Methods, 42:11 (1981) and Allum et al., supra at pp. 48–51).

It is apparent from the foregoing that the BR110 antibodies of the invention can be used in most assays involving antigen-antibody reactions. These assays include, but are not limited to, standard RIA techniques, both liquid and solid phase, as well as ELISA assays, immunofluorescence techniques, and other immunocytochemical assays (Sikora et al. (eds), Monoclonal Antibodies, pp. 32–52 (Blackwell Scientific Publications 1984).

ADMINISTRATION OF BR110 LIGANDS INTO ANIMALS

The BR110 ligands can be administered to animals in an amount sufficient to slow the proliferation of target cells or to kill them entirely. It would be clear to those skilled in the art that the optimal schedule for administering BR110 ligands will vary based upon the subject, the subject's height and weight, the severity of the disease (G. Goodman, et al., J. Clin. Oncol., 8, 1083 (1990). (Nedelman, M. A., Shealy, D. J., Boulin, R., Brunt, E., Seasholtz, J. I., Allen, E., McCartney, J. E., Warren, F. D., Oppermann, H., Pang, R. H. L., Berger, H. J. and Weisman, H. F. (1993) Rapid infant imaging with a Technetium-99m-labelled anti-myosin recombinant single-chain Fv: evaluation in a canine model of acute myocardial infarction. Journal of Nuclear Medicine 34, 234. Courtenay-Luck, N. S., and Epenetos, A. A. (1990). Targeting of monoclonal antibodies to tumors. Curr. Opinion Immunol. 2, 880–883). Ultimately, the use and schedule of administration will be decided by the treating physician. Clinical protocols for determining dosage range and scheduling are standard.

COMPOSITIONS INCLUDING THE ANTIBODIES OF THE INVENTION

The present invention provides compositions which comprise a monoclonal antibody of the invention to which a biologically or chemically active agent is attached.

In one embodiment, the biologically or chemically active agent is a toxin. The toxin is selected from a group which includes, but is not limited to, ricin, diphtheria toxin, pseudomonas, exotoxin-A, abrin, supporin, and gelonin.

Alternatively, the biologically and chemically agent comprises an enzyme, a drug, or a DNA fragment (Nedelman, M. A., Shealy, D. J., Boulin, R., Brunt, E., Seasholtz, J. I., Allen, E., McCartney, J. E., Warren, F. D., Oppermann, H., Pang, R. H. L., Berger, H. J. and Weisman, H. F. (1993) Rapid infant imaging with a Technetium-99m-labelled anti-myosin recombinant single-chain Fv: evaluation in a canine model of acute myocardial infarction. Journal of Nuclear Medicine 34, 234.

Attachment of the enzyme, drug, or DNA fragment to monoclonal antibodies is well known (Pollard-Knight, D., Hawkins, E., Yeung, D., Pashby, D. P., Simpson, M., McDougall, A., Buckle, P. and Charles, S. A. (1990) Immunoassays and nucleic acid detection with a biosensor based on surface plasmon resonance. Annales de Biologie Clinique 48, 642; Kronick, M. J. and Little, W. A. (1974) A new immunoassay based on fluorescent excitation by internal reflection spectroscopy. *Proceedings of the National Academy of Sciences USA* 71, 4553).

ADVANTAGES OF THE INVENTION

The antibodies of the present invention, like other antibodies which recognize human tumor-associated antigens, are additional members of the arsenal of diagnostic and therapeutic agents for the war on disease.

BR110 ligand is useful not only because it is a tumor specific antibody but also because it is an internalizing antibody. Antibodies of this type find use in therapeutic methods for selective cell killing utilizing antibody-drug or antibody-toxin conjugates ("immunotoxins") wherein a therapeutic antitumor agent is chemically or biologically linked to an antibody or growth factor for delivery to the tumor, where the antibody binds to the tumor-associated antigen or receptor with which it is reactive and "delivers" the antitumor agent inside the tumor cells (Embleton et al., "Antibody Targeting Of Anti-Cancer Agents", in *Monoclonal Antibodies For Cancer Detection and Therapy*, pp. 317–44 (Academic Press, 1985)).

In order that the invention described herein may be more fully understood, the following examples are set forth. It should be understood that these examples are for illustrative purposes only and are not to be construed as limiting the scope of this invention in any manner.

EXAMPLE 1
Preparation Of The BR110 Monoclonal Antibody

The BR110 monoclonal antibody of the invention was produced using hybridoma fusion techniques as described previously by M. Yeh et al., *Proc. Natl. Acad. Sci. USA*, (1979), supra and Yeh et al., *Int. J. Cancer* (1982), supra.

Briefly, BALB/c mice were immunized using neuraminidase pretreated H3922 human breast carcinoma cells ($10^7$ cells). The mice received multiple immunizations (x6). On the first occasion, the mice received intraperitoneal injection using RIBI adjuvant. On the second through sixth occasions, the mice were given one intraperitoneal injection using no RIBI adjuvant.

The total number of cells injected on each occasion was approximately $10^7$ cells. Four days after the last immunization, the spleen was removed and spleen cells were suspended in RPMI culture medium. The spleen cells were then fused with P2x63-Ag8.653 mouse myeloma cells in the presence of polyethylene glycol (PEG) and the cell suspension grown in microtiter wells in selective HAT medium as described by Yeh et al., supra [see, also, Kohler and Milstein, *Nature*, 256:495–97 (1975) and *Eur. J. Immunol.*, 6:511–19 (1976)]. The mixture was seeded to form low density cultures originating from single fused cells or clones.

The supernatants from these hybridoma cultures were then screened for direct binding activity on the cancer cell line, H3922, using an ELISA assay similar to that described by Douillard et al., "Enzyme-Linked Immunosorbent Assay For Screening Monoclonal Antibody Production Using Enzyme-Labeled Second Antibody", *Meth. Enzymol.*, 92:168–74 (1983).

According to this assay, antigen (with which the antibody being screened for is reactive) is immobilized on microtiter plates and then incubated with hybridoma supernatants. If a supernatant contains the desired antibody, the antibody will bind to the immobilized antigen and is detected by addition of an anti-immunoglobulin antibody-enzyme conjugate and a substrate for the enzyme which leads to a measurable change in optical density In the present studies, breast cancer cell line H3922 and human fibroblast were dispensed into a 96 well tissue culture plate (Costar, Cambridge, Mass.) and incubated overnight in a humid 37° C. incubator, 5% CO2.

The cells were then fixed with 100 μl of freshly prepared 2% paraformaldehyde, incubated for 15 min at room temperature, followed by blocking with specimen diluent (Genetic Systems, Seattle, Wash.) for 1 hr. at room temperature this being the incubation condition for the entire assay. After washing with P/BS hybridoma supernatants or purified antibody were then added and incubated for 1 hr. The plates were washed with PBS and a second step MAb (goat anti Mouse IgG/M, Tango Burlingname, Calif.) diluted in culture medium (IMDM, Gibco, N.Y. 10% FBS) was added and incubated for 1 hr. After a washing step buffered substrate (Genetic Systems) was added and the reaction was stopped with stopping reagent (Genetic Systems) after 15 min. incubation time. The absorbance was read at OD 450/630 nm (Dynatech Microelisa Autoreader).

The supernatants from the hybridoma cultures were then added at 100 μl/well, the wells incubated for 1 h at room temperature, and the cells washed three times with PBS. Next, goat anti-mouse horseradish peroxidase (Zymed, Calif.) diluted in 0.1% BSA and PBS was added to a concentration of 100 μl/well. The reaction mixture was incubated for either 1 h at room temperature or 30 min at 37° C. and the cells were then washed three times with PBS. o-phenylenediamine (OPD) was then added at 100 μl/well and the plates incubated in the dark at room temperature for 5–45 min.

Antibody binding to the cells was detected by a color change in the wells that occurred within 10–20 min. The reaction was stopped by adding 100 μl/well $H_2SO_4$ and the absorbance read in a Dynatech (Alexandria, Va. MICROELISA AUTOREADER assay device at 490 nm.

This assay can be performed using cultured adherent cells, live or with fixed, cells in suspension live or fixed, purified soluble antigen and cellular extracts as the immobilized antigen.

Hybridomas which produced antibodies with binding reactivity to the cancer cell line H3922 and not to human fibroblast were thus selected, cloned and the specificity of the subclones confirmed. The hybridoma culture was then expanded in vitro for antibody production. As disclosed above the BR110 antibody was purified from hybridoma supernatant by affinity chromatography on immobilized protein A (RepliGen, Cambridge, Mass.). Final formulation buffer was PBS and the antibody was sterile filtered and stored refrigerated or frozen at −70° C.

Hybridomas that were unreactive with PBLs were cloned, expanded in vitro, and further tested for antibody specificity. Those hybridomas producing antibody reactive with human breast cancer were recloned, expanded, and injected into pristane-primed 3-month old BALB/c mice, where they grew as ascites tumors.

Following this procedure, hybridoma cell line BR110 was obtained, cloned and injected into mice to develop as an ascites tumor. As disclosed above, the BR110 hybridoma has been deposited with the ATCC.

Monoclonal BR110 antibody was purified from ascites by affinity chromatography on immobilized recombinant protein A (Repligen, Cambridge, Mass.). Clarified ascites was diluted with an equal volume of binding buffer (1M potassium phosphate, pH 8) and applied to a protein A column previously equilibrated with binding buffer.

The column was extensively washed with binding buffer and then the antibody was eluted with 50 mM phosphoric acid, pH 3. The purified antibody fraction was neutralized with 1M Tris, pH 9 and then dialyzed against phosphate buffered saline. Purified BR110 ligand was finally sterile filtered and stored refrigerated or frozen.

EXAMPLE 2

Characterization of the BR110 monoclonal antibody
Isotype determination

To determine the class of immunoglobulin produced by BR110 hybridoma, the following ELISA technique was utilized: Dynatech Immulon 96 well plates were coated with goat anti-mouse IgG subclass antibodies (Southern Biotech, Birmingham, Ala.) at 1 $\mu$g/ml concentration in PBS and incubated overnight at 4° C.

Based on this procedure, it was determined that the BR110 monoclonal antibody is of the gamma 2a isotype.
Immunohistology The peroxidase-antiperoxidase (PAP) technique of L. A. Sternberger as described in *Immunochemistry*, pp. 104–69 (John Wiley & Sons, New York, 1979) and as modified by H. J. Garrigues et al., "Detection Of A Human Melanoma-Associated Antigen, p97, In Histological Sections Of Primary Human Melanomas", *Int. J. Cancer*, 29:511–15 (1982), was used for the immunohistological studies. The target tissues for these tests were obtained at surgery and frozen within 4 h of removal using isopentane precooled in liquid nitrogen.

Tissues were then stored in liquid nitrogen or at −70° C. until used. Frozen sections were prepared, air dried, treated with acetone and dried again [see Garrigues et al., supra]. Sections to be used for histologic evaluation were stained with hematoxylin.

To decrease non-specific backgrounds sections were pre-incubated with normal human serum diluted 1/5 in PBS (H. J. Garrigues et al., "Detection Of A Human Melanoma-Associated Antigen, p97, In Histological Sections Of Primary Human Melanomas", *Int. J. Cancer*, 29:511–15 (1982) ). Mouse antibodies, rabbit anti-mouse IgG, and mouse PAP were diluted in a solution of 10% normal human serum and 3% rabbit serum. Rabbit anti-mouse IgG (Sternberger-Meyer Immunochemicals, Inc., Jarettsville, Md.), was used at a dilution of 1/50. Mouse PAP complexes (Sternberger-Meyer Immunochemicals, Inc.) containing 2 mg/ml of specifically purified PAP was used at a dilution of 1/80.

The staining procedure consisted of treating serial sections with either specific antibody, i.e., BR110, or a control antibody for 2.5 h, incubating the sections for 30 min at room temperature with rabbit anti-mouse IgG diluted 1/50 and then exposing the sections to mouse PAP complexes diluted 1/80 for 30 min at room temperature. After each treatment with antibody, the slides were washed twice in PBS.

The immunohistochemical reaction was developed by adding freshly prepared 0.5% 3,3'-diaminobenzidine tetrahydrochloride (Sigma Chemical Co., St. Louis, Mo.) and 0.01% $H_2O_2$ in 0.05M Tris buffer, pH 7. 6, for 8 min (Hellstrom et al., *J. Immunol.*, 127:157–60 (1981)). Further exposure to a 1% $OsO_4$ solution in distilled water for 20 min intensified the stain. The sections were rinsed with water, dehydrated in alcohol, cleared in xylene, and mounted on slides. Parallel sections were stained with hematoxylin.

The slides were each evaluated under code and coded samples were checked by an independent investigator. Typical slides were photographed by using differential interference contrast optics (Zeiss-Nomarski). The degree of antibody staining was evaluated as 0 (no reactivity), + (a few weakly positive cells), ++ (at least one third of the cells positive), +++ (most cells positive), ++++ (approximately all cells strongly positive). Because differences between + and 0 staining were less clear cut than between + and ++ staining, a staining graded as ++ or greater was considered "positive". Both neoplastic and stroma cells were observed in tumor samples. The staining recorded is that of the tumor cells because the stroma cells were not stained at all or were stained much more weakly than the tumor cells.

Table 1 below demonstrates the immunohistological staining of various tumor and normal tissue specimens using the BR110 monoclonal antibody. As the tables clearly demonstrate, the BR110 antibody reacts with a wide range of human carcinoma specimens.

Binding assays

Recognition of cell surface antigens by the BR110 MAb was identified on a variety of carcinoma cell lines by immunofluorescence, using a Coulter Epics C FACS.

Single cell suspensions were aliquoted in culture medium (IMDM Gibco, N.Y., 10% FBS) at concentration of $5 \times 10^5$ to $1 \times 10^6$ cells. FITC conjugated BR110 MAb was added to the resuspended cell pellets at a 10 ug/ml concentration diluted in culture medium followed by an incubation of 1 hr. on ice. After washing the cells with culture medium the samples were analyzed for the mean florescence intensity. Binding ratios were calculated by dividing the linear fluorescence equivalent (LFE) by the LFE of the negative control. The results are shown in Table 4.

Determination of Antigen Binding sites per cell

Cell binding assays were performed with FITC conjugated BR110 MAb utilizing cells lines H3619 and H2987 followed by FACS analysis. Mean fluorescence intensity was determined upon staining with 2 fold dilutions of antibody 50 to 0.38 $\mu$g/ml). Fluorescinated beads with know size and intensity produced a standard curve which was included into the computation of fluorescence equivalents through antibody binding. The number of binding sites was determined for both cell lines to be $8 \times 10^4$ sites/cell.

EXAMPLE 3

Internalization of BR110

To determine whether BR110 could be internalized by antigen positive carcinoma cells with indirect inhibition assay utilizing a ricin A-chain conjugated antibody was applied.

According to this assay, the inhibition of H3-thymidine incorporation into cellular DNA is a measure of the cytotoxic effect of the given conjugate and reflects the internalization of ricin A-chain by the carcinoma cells.

Carcinoma cells were plated into a 96 well microtiter plate at $5 \times 10E3$ cells/well followed by an overnight incubation at 37° C., 5% $CO_2$. Hybridoma supernatant (neat and a 10 fold dilution) was added to the culture and incubated for 1 hour on ice. After washing with culture medium a goat anti-mouse IgG ricin A chain antibody (Inland Laboratories, Austin, Tex.) at 5 $\mu$g/ml concentration was added for an incubation time of 42 hrs. at 37° C. after which 50 ul of 3H-thymidine were added at 1 $\mu$Ci/well and the plate was incubated for another 6 hrs at 37° C. The assay plates were then frozen at −70° C. for several hours, thawed and the cells were harvested onto glass fibre filters (Wallac, Finland) using a cell harvester (Wallac, LKB). After adding scintillation counting liquid the filter matts were counted with a liquid scintillation counter (Wallac, LKB).

The results are expressed as the percentage of inhibition of H3-thymidine incorporation in the experimental group versus an untreated control Carcinoma cell line H3922 shows a 90% and H3396 a 60% growth inhibition after treatment with MAb BR110, the antibody exhibits evidence for internalization.

As another approach to study internalization of BR110, carcinoma cells were analyzed by confocal microscopy (Leica confocal laser scanning microscope).

Carcinoma cells (H3619, H3396, H3922) cultured in IMDM/10% FBS were allowed to adhere onto glass slides (NUNC chamber coverslips) for 48 hrs. The cells were placed at 4° C. for 15 min. FITC conjugated antibody BR110 or FITC conjugated antibody goat anti-mouse IgG (Tago, Burlingname, Calif.) as a control were added at a concentration of 10 ug/ml for 1 hr. at 4° C. Unbound antibody was removed by extensive washing with cold culture medium. To detect surface staining, the cells were washed with cold PBS and fixed with 2% paraformaldehyde for 15 min. at room temperature followed by a treatment with anti-fading reagent Dithioerythritol (Sigma).

To investigate internalization of BR110, culture medium at 37° C. was added and the cells were incubated for individual timepoints (0 time—3 hrs.) The time chase was terminated with cold PBS and post fixation. Images from the confocal microscope demonstrated that then cells were first exposed to BR110 at 4° C., the MAb bound exclusively to the cell surface. When the temperature was shifted to 37° C. and the cells kept at that temperature for 15 min. cytoplasmic staining was observed. The binding of BR110 at that time was unevenly distributed in cytoplasmic compartments and was largely absent from the cell surface. Neither the cell surface nor the cytoplasm was stained with the control MAb. The data demonstrate that the BR110 internalized into carcinoma cells.

We have tested MAb GA733 for internalization on carcinoma cell lines H3396 and SW948. The antibody bound exclusively to the cell surface at 4° C. with extremely weak or no internalization when tested at 37° C.

Antibody dependent and complement dependent cytotoxicity of BR110

ADCC and CDC test were carried out, labeling target cells (H3396, H3922) with $^{51}$Cr and exposing them for 4 h to human lymphocytes or human serum as a source of complement and BR110.

The release of $^{51}$Cr from the target cells was measured as evidence of tumor cell lysis (cytotoxicity).

BR110 was found to be negative for ADCC and CDC which may be attributed to its IgG2a isotype.

ELISA Competition

Taking in account the relatedness of the GA733 genes a competition assay was performed in order to establish the specificity differences between the MAbs BR110 and GA733. FACS analysis has shown that both proteins (GA733-1 and GA733-2) are present on the cell line H3396. Binding studies on paraformaldehyde fixed cells demonstrated that these antibodies do not crossblock and therefore bind to different epitopes.

Determination of the Avidity or Affinity

Scatchard analysis was performed in order to determine the avidity of radiolabeled BR110 MAb upon binding to adherent non-fixed cells. The data indicate that BR110 has an approximate association constant (Ka) of $5 \times 10^{-8}$ mol/liter tested on cell line H3619 and H3396.

Characterization of the BR110 antigen

BR110 antigen was isolated from the antigen positive carcinoma cell line H2987. The cells were solubilized in 1% Triton X-100 and the antigen-antibody complexes purified by protein A-Sepharose chromatography and SDS-Page under non-reducing conditions, and recovered by electroelution or electroblotting.

The Mr=66,000 protein was aminoterminally blocked. A single aminoterminal sequence of 20 residues was obtained for the Mr=55,000 protein, showing complete identity with the tumor-associated antigen GA733-1, residues 88–107.

Cyanogen bromide cleavage of the Mr=66,000 BR110 antigen generated one major fragment that was purified by SDS-Page, recovered by sequence was identical to the sequence of GA733-1 beginning at residue 63, preceded by a methionine residue. These data confirm that the BR110 antigen is amino-terminally blocked, fragmentation was required to obtain sequence information. In addition, the data suggest that the MR=55,000 glycoprotein is a natural cleavage product of the MR=66,000 protein that is still able to bind to MAb BR110.

The GA733-2 antigen was purified from the human colorectal carcinoma cell line SW948 and it partial amino acid sequence was determined (Linnenbach, A. J. et al., PNAS 86, 27–31, 1989). Two recombinants were isolated from a total human genomic library and the complete DNA sequence of the GA733-1 and GA733-2 gene determined.

The GA733-1 antigen which is recognized by MAb BR110 is closely related to the GA733-2 antigen (i.e. comparison of partial amino acid sequence [45 a.a] shows good homology) which is recognized by MAbs GA733 and CO17-1A.

Consequently, it appears that the BR110 MAb has specificity for a related, but unique antigen that is encoded by a gene that shares homology with exon 8 of the thyroglobulin type 1 repeat unit, HLA-DR associated invariant chain and the α subunit of the IL-2 growth factor receptor.

TABLE 1

| Mouse Mabs Immunohistology (number positive/number tested) | | | |
|---|---|---|---|
| | Mab | | |
| | BR110 | 13-66-6 | 13-66-7 |
| Carcinomas | | | |
| Lung | 25/28 | 25/28 | 25/28 |
| Colon | 18/28 | 17/25 | 17/25 |
| Breast | 22/23 | 19/22 | 20/22 |
| Ovarian | 17/18 | 17/18 | 17/18 |
| Melanoma | 0/9 | 0/9 | 0/9 |
| Normal Tissues | | | |
| Spleen | 0/12 | 0/7 | 0/7 |
| Liver | 0/11 | 0/11 | 0/3 |
| Kidney | 16/16(1) | 10/10(1) | 12/12(1) |
| Heart | 0/11 | 0/11 | 0/11 |
| Large intestine | 0/9 | 0/11 | 0/6 |
| Stomach | 0/13 | 0/14 | 0/14 |
| Esophagus | 7/7(2) | 5/5(2) | 5/5(2) |
| Pancreas | 10/10(3) | 9/9(3) | 6/6(3) |
| Lymph node | 0/5 | 0/5 | 0/5 |
| Adrenal | 0/7 | 0/7 | 0/7 |
| Ovary | 0/7 | 0/7 | 0/5 |
| Breast | 0/10 | 0/5 | 0/5 |
| Eye | 0/1 | 0/1 | 0/1 |
| Bladder | N/T | N/T | N/T |
| Thyroid | 0/9 | 0/5 | 0/5 |
| Skin | 9/9(4) | 6/6(4) | 7/7(4) |
| Brain | 0/10 | 0/7 | 0/7 |
| Lung | 19/24(5) | 11/12(5) | 14/14(5) |
| Tonsil | 2/2(2) | 2/2(2) | 2/2(2) |
| Prostate | 0/1 | 0/1 | 0/1 |
| Uterus | 0/5 | 0/5 | 0/5 |
| Small Intestine | 0/2 | 0/2 | 0/2 |

(1)only distal tubuli;
(2)weak staining of epithelium;
(3)weak staining of epithelium, no islet cells;
(4)stained epithelium;
(5)weak and diffuse staining.

TABLE 2

Immunohistology (number positive/number tested)

|  | MAb BR110 | GA733 |
|---|---|---|
| Carcinomas | | |
| Lung | 7/7 | 7/7 |
| Colon | 4/7 | 7/7 |
| Breast | 12/12 | 12/12 |
| Ovarian | 3/4 | 4/4 |
| Gastric | 3/8 | 8/8 |
| Normal Tissue | | |
| Large Intestine | 0/7 | 7/7 |
| Stomach | 0/3 | 2/3 (weak) |
| Esophagus | 6/6 | 0/6 |
| Pancreas | 2/2 | 2/2 |

TABLE 3

Mouse Monoclonal Antibodies
Immunohistology
Homogenous and heterogenous antigen expression
in tumor upon staining
Number positive/Number tested
Number Homogeneous
Number Heterogeneous

|  | Mab | | |
|---|---|---|---|
| Carcinoma | BR110 | 13-66-6-4 | 13-66-7 |
| Lung | 25/28 | 25/28 | 25/28 |
| Homo | 21 | 24 | 22 |
| Hetero | 4 | 1 | 3 |
| Ovarian | 17/18 | 17/18 | 17/18 |
|  | 12 | 12 | 11 |
|  | 5 | 5 | 6 |
| Colon | 18/28 | 17/25 | 17/25 |
|  | 12 | 9 | 8 |
|  | 6 | 8 | 9 |
| Breast | 22/23 | 19/22 | 20/22 |
|  | 20 | 17 | 17 |
|  | 2 | 2 | 3 |

TABLE 4

SURFACE ANTIGEN RECOGNITION BY MAb BR110
(DIRECT STAINING METHOD)

| FACS | Binding Ratio of FITC*-Mabs | | | |
|---|---|---|---|---|
| Cell line | Chi L6 | BR110 | 13-66-6 | 13-66-7 |
| breast ca. | | | | |
| H3396 | 1 | 12 | 9 | 13 |
| H3922 | 8 | 18 | 14 | 20 |
| H3464 | 66 | 1 | 1 | 1 |
| MCF-7* | 1.6 | 15 | 10.5 | 15.5 |
| H3630* | 1.7 | 15 | 12 | 18 |
| H3760* | 5 | 19 | 14 | 21 |
| adeno ca., colon | | | | |
| H3347 | 67 | 1 | 1 | 1 |
| H3719 | 34 | 1 | 1 | 1 |
| H3619* | 5 | 33 | 25 | 30 |
| H3737* | 2 | 20 | 15 | 21 |
| lung ca. | | | | |
| H2981 | 13.5 | 1 | 1 | 1 |
| H2987 | 6 | 20 | 16 | 24 |
| H3713* | 7 | 14 | 10 | 15 |
| H3754* | 29 | 25 | 18 | 26 |
| ovarian ca. | | | | |
| H3723B | 3 | 15 | 6 | 9 |
| H3907* | 16 | 37 | 30 | 46 |
| H3909* | 12 | 1 | 1 | 1 |
| CASKI* | 6 | 17 | 13 | 20 |
| Br. + Ov. ca. | | | | |
| H3730* | 12 | 23 | 18 | 18 |
| COS | 1 | 1 | 1 | 1 |

TABLE 5

SURFACE ANTIGEN RECOGNITION BY MAB BR110 AND MAB733
(INDIRECT STAINING METHOD)

| Cell Lines | BR110 Binding Ratios | GA733 |
|---|---|---|
| H2987 Lung ca. | 35 | 24 |
| H3922 breast ca. | 45 | 26 |
| H3396 breast ca. | 20 | 52 |
| SW94B colorectal ca. | 1 | 86 |

EXAMPLE 4

Internalization of the BR110 sFv-PE40 within carcinoma cells

Materials and Methods

Reagents and Cell Culture—Purified BR96 sFv-PE40 immunotoxin, used as a control, has been described previously (Friedman et al., 1993). Membrane binding ELISA's were performed using either rabbit polyclonal BR110 anti-idiotypic serum (Bristol Myers Squibb) or EXA2-1H8, a mouse anti-PE monoclonal antibody (Sigma Chemical Co. (St. Louis, Mo.). Specimen diluent and conjugate diluent were provided by Genetic Systems (Seattle, Wash.). Goat anti-mouse Ig (H+L)-specific HRP conjugate was purchased from Southern Biotechnology (Birmingham, Ala.). POROUS HQ RESIN chromatography matrix was purchased from Perceptive Biosystems (Framingham, Mass.). Restriction and DNA modifying enzymes were from New England Biolabs and [$^3$H]-leucine was purchased from New England Nuclear (Boston, Mass.). Other chemicals and reagents, including protease inhibitors and glutathione, were purchased from Sigma Chemical Co. (St. Louis, Mo.). H3619 colon adenocarcinoma, H3754 lung carcinoma and H3907 ovarian carcinomas were cultured in Iscoves modified Dulbecco's medium (IDMEM) with 10% fetal calf serum. The MCF-7 breast carcinoma cell line was obtained from the ATCC and cultured as described above. The BR110 monoclonal antibody (mAb) was developed by immunization of mice with the human breast carcinoma cell line H3922 according to established procedures.

Amino Terminal Sequencing

Approximately 10 nmoles of muBR110 IgG, purified from continuous hybridoma cell culture, was separated by 15% SDS-PAGE, and the heavy and light chains were isolated for NH$_2$-terminal sequence analysis using an Applied Biosystems 477 PROTEIN SEQUENCER® and an Applied Biosystems 120 PTH ANALYZER® (Hewick et al, 1981; Matsudaira, P., 1987). Twenty-five cycles of Edman degradation were performed. However, amino terminal sequence was only obtained for the light chain, as the heavy chain was thought to be N-terminally blocked.

RNA Isolation, cDNA Synthesis, and Amplification

RNA was prepared from 5×10$^7$ muBR110 hybridoma cells as described previously (P. Chomezynski and N. Sacchi, 1987). cDNA was obtained using total RNA and the thermostable rth polymerase ($r^{TH}$-RT-RNA-PCR Kit®, Perkin Elmer Cetus) according to manufacturer's instructions. For amplification of the heavy chain $F_v$ gene we used the primer pair, MHV P9 (MHV=Mouse Heavy Variable Region; 5'-ACTACAC<u>GGTACC</u>CGGGATC-CATGG$^C/_A$TTGGA$^A/_C$CTGCTATTCCTG-3')(SEQ. ID NO:1)(Jones and Bendig 1991) and the 3' $V_H$ constant primer (5'-N6<u>GAATTCA</u>$^T/_C$C-TCCACACACAG-G$^A/_G$$^A/_G$CCAGTGGATAGAC-3')(SEQ. ID NO:2, (Larrick, et al., 1991). The 5' primer for the variable light chain gene was designed according to the N-terminal amino acid sequence derived from Edman degradation and database alignment to other related mouse light chain genes. The 5' primer was (5'CGATCC<u>GAATTC</u>GACATTGTGATGACCCAGTCTCA 3')(SEQ. ID NO:3) while the 3' $V_L$ constant primer was mck-3 (5'-N4 <u>GAATTC</u>CAAGAAGCACACGACTGAGGCA-3')(SEQ. ID NO:4)(Gilland et al., 1991). The recognition sequences for Kpn I and EcoR I are underlined.

Cloning of Amplified cDNA

The products of the amplification of heavy- and light-chain Fv encoding DNA fragments were identified by agarose gel electrophoresis and migrated with an apparent molecular size of 475 and 375 base pairs respectfully. At their 5' and 3' ends are restriction endonuclease recognition sites KpnI and EcoRI for cloning the PCR products into pBluescript SK(+) (Stratagene, La Jolla, Calif.). The nucleotide sequence was determined for multiple clones of BR110 heavy and light-chain gene segments using double-stranded plasmid DNA as template and the Sequenase 2.0 reagent kit® (United States Biochemical, Cleveland, Ohio) with T7 and T3 sequencing primers (Pharmacia, Piscataway, N.J.).

BR110 sFv.PE40 Expression Plasmid Construction

The expression plasmid used for production of BR110sFv.PE40 in *E. coli* utilizes the bacteriophage T7 RNA polymerase promoter (Studier and Moffat, 1986). The BR110 V regions were PCR amplified in order to modify their terminal restriction sites using a 5' $V_H$ PCR primer (5'-GCA ATG <u>CATATG</u>CAG ATC CAG TTG GTG CAG TCT GGA C-3') (SEQ. ID NO:5) which encoded the Nde I restriction site, underlined, which includes an ATG translation initiation code (bold) and the first eight codons of the $V_H$ gene. The 3' $V_L$ PCR primer (5'-CCA TGG <u>ATG CAT</u> CCG TTT CAG CTC CAG CGT GGT CCC AGC-3') (SEQ. ID NO:6) which encoded the Nsi I restriction site (underlined) and the last nine codons of the $V_1$ gene. We also inserted a flexible linker, $(Gly_4Ser)_3$ between the two V domains (Huston et al., 1988; Chaudhary et al., 1989) by synthesizing the 3' $V_H$ PCR primer (5'-CCG GCC <u>GGA TCC</u> GCC TCC GCC TGA TGA GGA GAC GGT GAC CGT GGT CCC T-3')(SEQ ID NO:7) which was designed to have the Bam H I restriction site (underlined) the first half of the linker (bold) and the last eight codons of the $V_H$ gene. The 5' $V_L$ PCR primer (5'-CCG GCC <u>GGA TCC</u> GGC GGT GGC GGT TCT GGC GGT GGC GGT TCT GAC ATT GTG ATG ACC CAG TCT CAC-3') (SEQ. ID NO:8) encodes the Bam H I restriction site (underlined) the second half of the linker (bold) and the first eight codons of the $V_L$ gene. The Bam H I restriction site was used to ligate the two PCR products together and was then reamplified via PCR using the 5' $V_H$ and 3' $V_L$ primers (Sambrook et al., 1989). The BR110 sFv was then substituted for the BR96 sFv (McAndrew, 1995), in pBW7.0, a pMS8 (+) based vector, by NdeI+Nsi I digestion followed by ligation. The resulting expression plasmid directs the fusion protein pBR110sFv-PE40 to the cytoplasm and was confirmed by DNA sequence analysis.

Expression and Purification of BR110 sFv-PE40

The single-chain immunotoxin fusion protein BR110 sFv-PE40 was expressed in *E. coli* as described above. *E. coli* BL21 (IDE3) cells (Studier & Moffat, 1986) were transformed with expression plasmid pBR110sFv-PE40, grown in "Terrific-Broth" medium (Gibco-BRL, Gaithersburg, Md.) containing 100 ug/ml ampicillin at 37° C. and induced with 1 mM IPTG in the logarithmic phase at an OD650 of 1.0. The cells were harvested ninety minutes later. For analytical analysis, 1 ml samples were harvested by centrifugation and osmotically shocked in cold $H_2O$ for 10 min. The cells were centrifuged again and the cell pellets were resuspended in 10 mM Tris-HCL, pH 7.4. Aliquots prepared from approximately 10$^8$ spheroplasts were subjected to SDS-PAGE and stained (Laemmli, 1970) or subjected to immunoblot analysis using the rabbit anti-BR110 idiotypic polyclonal sera. A bulk bacterial cell pellet prepared from 6 L shake flask was processed as described above and inclusion bodies were isolated as previously described (Friedman et al., 1993). Extensively washed inclusion bodies were then denatured in 7M guanidine.

Antigen Cloning, Expression and Purification

The BR110 antigen (GA733-1) was isolated from H2987 cells and aminoterminal sequence of 20 residues was obtained. The residues were complementary to the 88–107 residues of the tumor-associated antigen GA733-1. GA733-1 is a gene sequence isolated based on its homology to GA733-2, which encodes the gastrointestinal-associated antigen recognized by Mabs GA73.3 and CO17-1A. The GA733-1 is 50% homologous to the GA733-2 antigen.

Northern analysis was performed on three carcinoma cell lines, H3907 ovarian carcinoma, H3619 colon adenocarcinoma and H3754 lung carcinoma, that had been shown to express the BR110 antigen GA733-1 via FACS analysis. RNA was isolated from 20–30 million cells of each using the Chomczynski and Sacchi method (Chomczynski and Sacchi, 1987 (Anal. Biochem 162:156–159)). An oligonucleotide probe was made based on the known nucleotide sequence of GA733-1. Northern analysis was conducted as described in Mantianis.

The cDNA of the antigen was isolated using sequence specific primers, total RNA and Reverse-transcriptase polymerase (RT-RNA PCR, Perkin Elmer Cetus) according to manufacturer's instructions except for the addition of 10% DMSO, used because the antigen GA733-1 is greater than 50% GC rich. The specific RT primers used were 110-FP (5' GCC <u>AAG CTT</u> GTC CGG TCC GCG TTC CTC CGC CCC ACC 3')(SEQ. ID NO:9), 110-RP (5' CGG TCT AGA <u>CTC GAG</u> GCC GGG TAC CTA CAA GCT CGG TTC 3')(SEQ ID NO:10), 110-RP1 (5' GCG <u>GGG ATC CGT</u> GAG GCG CTT CAT GGA GAA CTT CGG 3')(SEQ ID NO:11). The restriction site for each primer is underlined and are Hind III, Xho I, and Bam HI respectively. Subsequent to the reverse transcription with either Random Hexanucleotides provided with the kit or the 3' 110-RP1 primer, 32 PCR cycles were conducted with appropriate sized products recovered. The 1.15 kB gene fragments were digested with Hind III and Bam HI prior to ligation into pCD40ThrRg1 (in a CDM7 Background) while the 0.86 kB gene fragments were ligated as HindIII-XhoI fragments into pCDM8. Plasmid DNAs containing the appropriate-sized inserts were identified and submitted for DNA sequence analysis. The DNA fragment encoding the extracellular domain was subcloned upstream of the human Fc region and transiently expressed in COS cells. The resulting fusion protein was purified by Protein-A affinity Chromatography.
Cell membrane ELISA Membranes from H3619 colon adenocarcinoma cells were prepared (Spira et al., "The Identification Of Monoclonal Class Switch Variants By Subselection And ELISA Assay", *J. Immunol. Meth.*, 74:307–15 (1984), Uotila et al., "Two-Site Sandwich ELISA With Monoclonal Antibodies To Human AFP", *J. Immunol. Methods*, 42:11 (1981), Sikora et al. (eds), *Monoclonal Antibodies*, pp. 32–52 (Blackwell Scientific Publications 1984)).

Membranes were coated on the surface of Immulon II 96® well plates (Dynatech Labs, Chantilly, Va.) at 10 ug/ml protein in 0.5M sodium carbonate/sodium bicarbonate, pH 9.6 and incubated overnight at 4° C. The plates were washed three times with PBS, blocked with specimen diluent at 1:10 (Genetic Systems, Seattle, Wash.) for 1 hr at RT. The plates were washed three times with PBS and then incubated with primary antibody overnight at 4° C. in conjugate diluent (Genetic Systems, Seattle, Wash.). The plates were then washed three times with PBS followed by the addition of secondary antibody, either goat anti-mouse IgG specific HRP or polyclonal rabbit BR110 anti-idiotypic antibodies, at 2.5 ug/ml in conjugate diluent. The plates were incubated for 1 hr at RT and then washed three times with PBS. The plates were washed three times with PBS, then either incubated for 1 hr at RT with goat anti-rabbit IgG Fc specific HRP at 1:1000 in conjugate diluent or washed an additional two times after which the reaction was developed with tetramethyl benzidine (TMB) for 15 minutes at RT and stopped with 1.3M $H_2SO_4$. After incubation the polyclonal sera plates were also washed five times in PBS and treated as stated above. The absorbency was quantified at dual wavelength 450/630 nm, using a Bio-tek microplate reader (Winooski, Vt.).
Cytotoxicity Analysis Cells were incubated with BR110 sFv-PE40 for 24 h at 37° C. The wells were then washed two times with phosphate buffered saline (PBS), 200 ul/well of 1.5 uM calcein-AM (Molecular Probes, Inc., Eugene, Oreg.) was added, and the plates were incubated for 40 minutes at RT. Calcein-AM is membrane permeable and non-fluorescent. When hydrolysis occurs by intracellular esterases, the intensely fluorescent product calcein is formed. At the end of the incubation, the fluorescence is measured using a Fluorescence Concentration Analyzer® (Baxter Heathcare Corp., Mundelein, Ill.) at excitation/emission wavelengths of 485/530 nm.

EXAMPLE 5

BR110 sFv-PE40 Inmunotoxin Construction (pSE 70.0)

The original BR110 sFv-PE40 construct was subcloned into a vector that contains the kanamycin resistance gene and a second lac repressor built into the expression vector. This was done by digesting pET29c (Novagen Inc) with EcoRI and XbaI and inserting a similarly digested BR110 sFv-PE40 between the two sites. The resulting construct was named pSE 70.0 (FIG. 1) and was under the control of the T7 promoter.

BR110 sFv-PE40 Expression, Refolding, and Purification

The single-chain immunotoxin fusion protein BR110 sFv-PE40 was expressed in *E. coli* as inclusion bodies. Cell paste from 1 liter of starting culture containing expressed BR110 sFv-PE40 fusion protein was resuspended in 50 mM Tris-HCl pH 8.0+1 mM EDTA. The sample was centrifuged at 8K for 15 minutes and the supernatant was decanted. The pellet was resuspended in 40 ml $H_2O$, kept at 4° C. for 10 min. and centrifuged at 8K for 15 min. The pellet was resuspended in 50 mM Tris-HCl pH 8.0+1 mM EDTA. 0.5 mg/ml of lysozyme was added to a final concentration of 0.25 mg/ml. The sample was kept on ice for 30 min.

The detergent Tergitol was then added to the sample to a final concentration of 4%. The sample was kept on ice for 60 min. and centrifuged at 18K for 30 min. The sample was washed three times with 50 mM Tris-HCl+1 mM EDTA. The pellet was sonicated in 3 ml of guanidine solution (7M guanidine-HCl, 0.1M Tris-HCl pH 7.4, 5 mM EDTA) and left at 4° C. for 48 hr. The sample was then centrifuged at 30K for 30 min. and the supernatant was collected. The sample was then refolded at 100 ug/ml by slow addition to refold buffer (0.1M Tris-HCl pH 8.0, 5 mM EDTA, 1 mM GSSH, 1 uM GSH, 1M urea). The refolded protein was kept at 4° C. for 48 hrs and dialyzed against 40 mM HCl pH 8.0 until the conductivity was below 5 mS/cm. The sample was loaded onto a DEAE anion exchange column and eluted with a linear gradient of 40 mM Tris-HCl pH 8.0+1M NaCl. The fractions corresponding to a 67 kDa BR110 sFv-PE40 fusion protein by non-reducing SDS-PAGE were collected, diluted in 250 ml of 40 mM Tris-HCl pH 8.0 and reapplied to a Mono-Q anion exchange column with the same NaCl gradient as for the DEAE column. The samples corresponding to monomer BR110 sFv-PE40 were collected and quantitated by the Coomassie-Plus assay (Pierce Chem Co.).
BR110-BD1 Immunotoxin Construction and Purification BR110 mAb was thiolated by addition of 3-fold molar excess 2-iminothiolane in 0.2M sodium phosphate buffer (pH 8.0), 1 mM EDTA for 1 h at 37° C. BD1 was derivatized with 3-fold molar excess SMPT (4-succinimidyloxycarbonyl-a-methyl-a-(2-pyridyldithio)-toluene) in 0.2M sodium phosphate buffer (pH 8.0), 1 mM EDTA at room temperature for 60 min. BR110-BD1 was applied to a size-exclusion column (TSK-3000) and separated from free toxin. The immunotoxin (180 kDa) and free antibody (150 kDA) eluted together and were further purified by Blue-Sepharose affinity chromatography. BR110-BD1, in 0.1M sodium phosphate pH 7.0 (wash buffer), was absorbed to Blue-Sepharose (5 ml resin/5 mg conjugate) for 16 h at 4° C. The mixture was packed in a 5 ml Econocolumn (Bio-Rad, Richmond, Calif.), and 1 ml fractions were eluted with a 2-step gradient of increasing NaCl concentrations in wash buffer (400 mM NaCl, step 1; 800 mM NaCl, step 2). The immunotoxin conjugate was quantitated at $OD_{280}$ (1.4=1 mg/mi) and analyzed by non-reducing SDS-PAGE.
Cytotoxicity Analysis of BR110-Immunotoxins Tumor cells ($10^5$ cells/ml) in growth medium were added to 96-well flat bottom tissue culture plates (0.1 ml/well) and incubated at 37° C. for 16 h. Dilutions of BR110 sFv-PE40 or BR110-BD1 were made in leucine-free RPMI (assay medium) and 0.1 ml was added to each well for 20 h at 37° C. (for BR110 sFv-PE40) or for 20 and 44 h (for BR110-BD1). The cells were pulsed with [$^3$H]-leucine (1 uCi/well) for an additional 4 h at 37° C. The cells were lysed by freeze-thawing and harvested using a Tomtec cell harvester (Orange, Conn.). Incorporation of [$^3$H]-leucine into cellular protein was determined using an LKB Beta-Plate liquid scintillation counter.

Excess BR110 IgG (50 ug/ml) was added to the 48 hour BR110-BD1 cytotoxicity study to demonstrate BR110 specificity in the assay. Except for the addition of the BR110 IgG, the assay was done exactly as stated above.

TABLE 6

BR110 sFv-PE40 24 hr. Cytotoxicity and FACS analysis on selected cell lines

| Cell Line | BR110 sFv-PE40 EC$_{50}$ | BR110 FACS binding ratio |
| --- | --- | --- |
| H2987 | 0.7 ng/ml | 18.28 |
| MCE-7 | 2.85 ng/ml | 13.17 |
| H3396 | 9 ng/ml | 17.1 |
| H2981 | >1 ug/ml | 1 |

TABLE 7

BR110 IgG-SMPT-BD1 Conjugate Activity on Various Carcinoma Cell Lines. 24 and 48 hour Incubation.

| Cell Line | FACS (BR110) | 24 hr EC$_{50}$ (ug/ml) | 48 hr EC$_{50}$ (ug/ml) | 48 hr +BR110 (50 ug/ml) |
| --- | --- | --- | --- | --- |
| H3619 | 33 | 0.07 | 0.06 | 2 |
| H2987 | 20 | 0.1 | 0.001 | 4 |
| MCF-7 | 15 | 5 | 0.05 | >5 |
| H3396 | 12 | nd | 0.09 | >5 |
| H2981 | 1 | >5 | >5 | >5 | nd = not done

---

What is claimed is:

1. A monoclonal antibody that binds to GA733-1 antigen, said antibody having an antigen binding site which competitively inhibits the binding of monoclonal antibody BR110 produced by a hybridoma designated ATCC No. HB11698 to the GA733-1 antigen.

2. The antibody of claim 1, wherein the antibody preferentially binds tumorigenic tissue of a cell lineage but does not bind normal tissue of the same lineage.

3. The antibody of claim 1, wherein the antibody forms a complex with the GA733-1 antigen on the surface of a cell and is subsequently internalized into the cell.

4. The antibody of claim 1, wherein the antibody binds colon carcinoma tissue but does not bind normal intestine tissue.

5. The antibody of claim 1, wherein the antibody binds breast carcinoma tissue but does not bind normal breast tissue.

6. The antibody of claim 1, wherein the antibody does not bind normal liver, breast or thyroid tissue.

7. A hybridoma which produces the monoclonal antibody of claim 1.

8. A hybridoma designated ATCC No. HB11698.

9. A conjugate comprising the antibody of claim 1 joined to a cytotoxic agent.

10. The conjugate of claim 9, wherein the cytotoxic agent is an enzyme, lymphokine, oncostatin or toxin.

11. The monoclonal antibody of claim 1 labeled with a detectable marker.

12. The monoclonal antibody of claim 11, wherein the detectable marker is an enzyme, a paramagnetic isotope, biotin, a fluorophore, a chromophore, a heavy metal, or a radioisotope.

13. An Fv molecule comprising the antigen binding site of the monoclonal antibody of claim 1.

14. The Fv molecule of claim 13 which is an sFv molecule.

15. An Fab molecule comprising the antigen binding site of the monoclonal antibody of claim 1.

16. An Fab' molecule comprising the antigen binding site of the monoclonal antibody of claim 1.

17. An F(ab')$_2$ molecule comprising the antigen binding site of the monoclonal antibody of claim 1.

18. A bispecific antibody with a binding specificity for two different antigens, one of the antigens being that with which the monoclonal antibody of claim 1 binds.

19. A recombinant antibody, comprising human constant regions and murine antigen-binding region, wherein the antibody competitively inhibits the binding of monoclonal antibody BR110 produced by hybridoma HB 11698 to the GA733-1 antigen.

20. A composition comprising a monoclonal antibody of claim 1 to which a therapeutic agent is attached.

21. The composition of claim 20, wherein the therapeutic agent is a cytotoxic agent which comprises a toxin selected from the group consisting of ricin, diphtheria toxin, bryodin, pseudomonas, exotoxin-A, abrin, saporin, and gelonin.

22. The composition of claim 20, wherein the therapeutic agent comprises an enzyme, a drug, or a nucleic acid.

* * * * *

UNITED STATES PATENT AND TRADEMARK OFFICE
CERTIFICATE OF CORRECTION

PATENT NO. : 5,840,854

DATED : November 24, 1998

INVENTOR(S) : Hellstrom et al.

It is certified that error appears in the above-identified patent and that said Letters Patent is hereby corrected as shown below:

On the title page:

Item [73]: Address of Assignee, delete "Princeton, N.J." and insert —New York, NY—

Column 3, line 38, delete "ATTC" and insert —ATCC—

Column 5, line 66, delete "The" and insert —In—

Signed and Sealed this

Twentieth Day of April, 1999

*Attest:*

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ACTACACGGT ACCCGGGATC CATGGMTTGG AMCTGCTATT CCTG                    44
```

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GAATTCAYCT CCACACACAG GRRCCAGTGG ATAGAC                             36
```

( 2 ) INFORMATION FOR SEQ ID NO:3:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

CGATCCGAAT TCGACATTGT GATGACCCAG TCTCA    35

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GAATTCCAAG AAGCACACGA CTGAGGCA    28

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GCAATGCATA TGCAGATCCA GTTGGTGCAG TCTGGAC    37

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CCATGGATGC ATCCGTTTCA GCTCCAGCGT GGTCCCAGC    39

( 2 ) INFORMATION FOR SEQ ID NO:7:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCGGCCGGAT CCGCCTCCGC CTGATGAGGA GACGGTGACC GTGGTCCCT    49

( 2 ) INFORMATION FOR SEQ ID NO:8:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

| CCGGCCGGAT | CCGGCGGTGG | CGGTTCTGGC | GGTGGCGGTT | CTGACATTGT | GATGACCCAG | 60 |
| TCTCAC | | | | | | 66 |

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

| GCCAAGCTTG | TCCGGTCCGC | GTTCCTCCGC | CCCACC | 36 |

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| CGGTCTAGAC | TCGAGGCCGG | GTACCTACAA | GCTCGGTTC | 39 |

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

| GCGGGGATCC | GTGAGGCGCT | TCATGGAGAA | CTTCGG | 36 |

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

Leu   Glu   Leu   Lys   Arg
                5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

Met His Gly Thr Lys Leu
                      5

( 2 ) INFORMATION FOR SEQ ID NO:14:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:14:

Met Ala Glu Glu Gly
                  5